US006506727B1

(12) United States Patent
Hansson et al.

(10) Patent No.: US 6,506,727 B1
(45) Date of Patent: Jan. 14, 2003

(54) NERVE REGENERATION

(75) Inventors: Hans-Arne Hansson, Hovas (SE); Samuel E. Lynch, Beverly, MA (US); Harry N. Antoniades, Newton, MA (US)

(73) Assignee: Institute of Molecular Biology, Inc., Boston, MA (US)

( * ) Notice: Subject to any disclaimer, the term of this patent is extended or adjusted under 35 U.S.C. 154(b) by 0 days.

(21) Appl. No.: 08/198,542

(22) Filed: Feb. 18, 1994

Related U.S. Application Data

(63) Continuation of application No. 07/797,315, filed on Nov. 25, 1991, now abandoned.

(51) Int. Cl.$^7$ .............................................. A61K 38/18
(52) U.S. Cl. ..................................... 514/12; 530/399
(58) Field of Search .......................... 514/2, 8, 12, 21

(56) References Cited

U.S. PATENT DOCUMENTS

| 4,775,073 A | | 10/1988 | Udagawa | |
|---|---|---|---|---|
| 4,861,757 A | | 8/1989 | Antoniades et al. | |
| 4,878,913 A | * | 11/1989 | Aebischer | 623/12 |
| 5,019,559 A | | 5/1991 | Antoniades et al. | |
| 5,068,224 A | * | 11/1991 | Fryklund | 514/21 |
| 5,093,317 A | | 3/1992 | Lewis et al. | 514/12 |
| 5,656,605 A | * | 8/1997 | Hansson et al. | 514/21 |

FOREIGN PATENT DOCUMENTS

| WO | WO87/01728 | * | 3/1987 |
|---|---|---|---|
| WO | WO-A-90 14838 | | 12/1990 |

OTHER PUBLICATIONS

*The Chemical Abstracts*, 104, 153, 1986, Abstr. No. 62860e.*
The Chemical Abstracts, 102, 392, 1985, abst. No. 43762s.*
Morrison et al., Proc. Natl. Acad. Sci., 83, 7537–7541, 1986.*
Gospodarowicz et al., *Journal of Cellular Physiology Suppl.* 5, 15–26, 1987.*
*The Merck Manual*, 16$^{th}$ Edition, Rahway, NJ, 1992, pp. 1512–1513.*
Jackowski, A., *British Journal of Neurosurgery,* 9: 303–317, 1995.*
Henderson, Z., *Progress in Neurobiology,* 48: 219–254, 1996.*
Smits et al., Proc. Natl. Acad. Sci. USA 88:8159–8163, 1991.
Cordeiro et al., Plastic and Reconstructive Surgery 83:1013–1019.
Lynch et al., The Journal of Clinical Investigation 84:640–646, 1989.
Sjoberg et al., Brain Research 485:102–108, 1989.
Lynch et al., Proc. Natl. Acad. Sci. USA 84:7696–7700, 1987.
Yeh et al., Cell 64:209–216, 1991.
Lynch et al., J. Peridontol 62:458–467, 1991.
Bondy et al., Molecular Endocrinology 9:1386–1398, 1990.
Eccleston et al., European Journal of Neuroscience, 2;985–992, 1990.
Nachemson et al., Growth Factors 3:309–314, 1990.
Seckel, Muscle & Nerve 13:785–800, 1990.
Claesson–Welsh et al., Proc. Natl. Acad. Sci. USA 86:4917–4921, 1989.
Claesson–Welsh et al., Journal of Biological Chemistry 264:1742–0747, 1989.
Daughaday et al., Endocrine Reviews 10:68–91.
Hoppe et al., Biochemistry 28:2956–2960, 1989.
Lynch et al., J. Clin Periodontol 16:545–548, 1989.
Matsui et al., Science 243:800–804, 1989.
Raff, Science 243:1409–1524, 1989.
Canalis et al., J. Endocrinol Invest 12:577–584, 1989.
Pringle et al., The EMBO Journal 8:1049–1056, 1989.
Andersson et al., Acta Physiol Scand 132:167–173, 1988.
Baxter, Comp. Biochem. Physiol. 91B:229–235, 1988.
Baskin et al., TINS 11:107–111, 1988.
Dodd et al., Science 242:692–699, 1988.
Han et al., Journal of Clinical Endocrinology and Metabolism 66:422–429, 1988.
Hansson et al., Acta Physiol Scand 132:35–41, 1988.
Hart et al., Science 240:1529–1531, 1988.
Heldin et al., EMBO Journal 7:1387–1393, 1988.
Kanje et al., Brain Research 475:254–258, 1988.
Noble et al., Nature 333:560–562, 1988.
Pinto et al., Journal of Neuroscience Research 19:312–320, 1988.
Richardson et al., Cell 53:309–319, 1988.
Aizenman et al., Brain Research 406:32–42, 1987.
D'Ercole, Journal of Developmental Physiology, 9:481–495, 1987.
Han et al., The Journal of Neuroscience 7:501–511, 1987.
Hansson et al., Cell Tissue Res. 247:241–247, 1987.
Morgan et al., Nature 329:301–307, 1987.
Muller et al., Brain Research 413:320–326, 1987.
Schofield et al., Development 101:793–803, 1987.
Shemer et al., The Journal of Biological Chemistry 262:7693–7699, 1987.
Sara et al., Proc. Natl. Acad. Sci. USA 83:4904–4907, 1986.
McMorris et al., Proc. Natl. Acad. Sci. USA 83:822–826, 1986.
Ullrich et al., The EMBO Journal 5:2503–2512, 1986.
Yarden et al., Nature 323:226–232, 1986.
Betsholtz et al., Nature 320:695–699, 1986.
Foehring et al., Journal of Neurophysiology 55:947–965, 1986.

(List continued on next page.)

Primary Examiner—Marianne P. Allen
(74) *Attorney, Agent, or Firm*—Clark & Elbing LLP

(57) ABSTRACT

It has been found that the growth factor PDGF, when used in combination with another growth factor such as IGF-I, acts synergistically with the other factor to promote neuronal regeneration.

5 Claims, 1 Drawing Sheet

OTHER PUBLICATIONS

Figure 1:
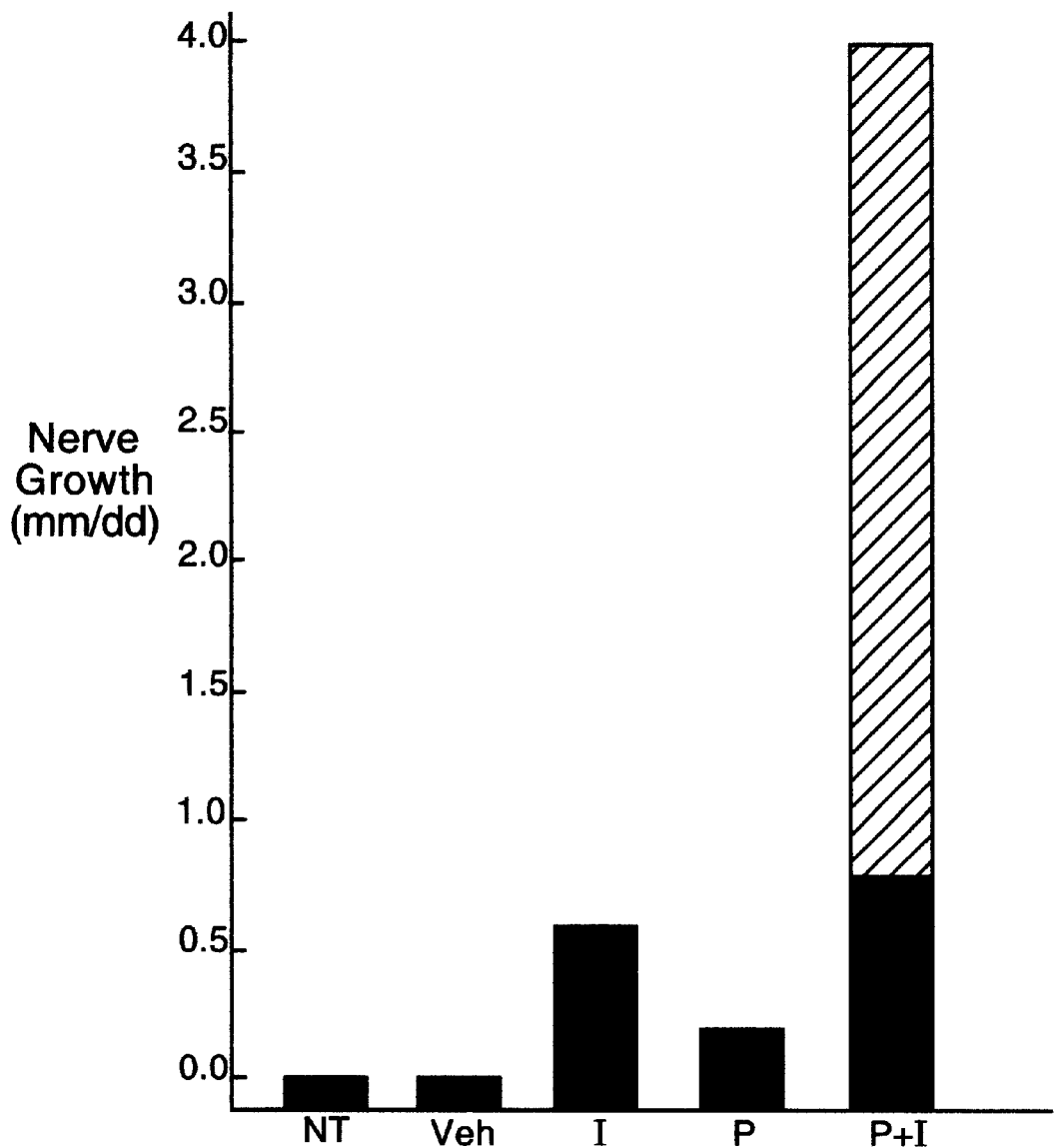

Mattsson et al., The Journal of Cell Biology 102:1949–1954, 1986.
Recio–Pinto et al., The Journal of Neuroscience 6(5):1211–1219, 1986.
Hansson et al., Acta Physiol. Scand. 126:609–614, 1986.
Hannink et al., Molecular and Cellular Biology 6(4):1343–1348, 1986.
Gordon et al. (eds.) The Current Status of Peripheral Nerve Regeneration, pp. 79–88, 1988.
Seckel et al., Plastic and Reconstructive Surgery 78:793–798, 1986.
Rao et al., Proc. Natl. Acad. Sci. USA 83:2392–2396, 1986.
Williams et al., in *The Current Status of Peripheral Nerve Regeneration*. Gordon et al. (eds.), pp. 111–122, 1988.
D'Ercole et al., Pediatric Pulmonology, 1:s99–s106, May–Jun. Suppl. 1985.
Froesch et al., Ann. Rev. Physiol. 47:443–467, 1985.
Williams et al., The Journal of Comparative Neurology 231:209–220, 1985.
King et al., Proc. Natl. Acad. Sci. USA 82:5295–5299, 1985.
Antoniades et al., Cancer Cells 3/Growth Factors and Transformation 145–151, Jun. 1985.
Madison et al., Experimental Neurology 88:767–772, 1985.
Bothwell, Journal of Neuroscience Research 8:225–231, 1982.
Van Wyk in *Hormonal Proteins and Peptides*. Choh Hao Li, ed., vol. XII, chapter 3, pp. 81–125, 1984.
Owen et al., Science 225:54–56, 1984.
Clarke et al., Nature 308:464–467, 1984.
Stroobant et al., The EMBO Journal 12(3):2963–2967, 1984.
Devare et al., Cell 36:43–49, 1984.
Gazit et al., Cell 39:89–97, 1984.
Wang et al., The Journal of Biological Chemistry 259(17):10645–10648, 1984.
Humbel in *Hormonal Proteins and Peptides*. Choh Hao Li, ed. vol. XII, chapter 3, pp. 57–79, 1984.
Robbins et al., Nature 305:605–608, 1983.
Waterfield et al., Nature vol. 304:35–39, 1983.
Gordon, Somatic and autonomic nerve–muscle interactions, Chapter 10:289–325, 1983.
Antoniades, Science 220:963–965, 1983.
Doolittle et al., Science 221:275–277, 1983.
Favera et al., Science 218:686–688, 1982.
Light et al., Sicnece 213:1532–1534, 1981.
Gundersen et al., The Journal of Cell Biology 87:546–554.
Lundborg et al., The Journal of Hand Surgery 5:35–38, 1980.
Lundborg et al., Brain Research 178:573–576, 1979.
Grafstein et al., Neuronal Plasticity, 1978.
Haftek et al., J. Anat. 103:233–243, 1968.
Sasahara et al., Cell, vol. 64, Jan. 11, 1991, pp. 217–227.
Valenzuela et al., "Roles of patelet–derived growth factor in the developing and mature nervous systems", Brain Research Reviews, vol. 24 (1997) pp. 77–89.*
Bögler et al., Proc. Natl. Acad. Sci., USA, vol. 87, pp. 6368–6372, Aug./90.
Eccleston et al., European Journal of Neuroscience, 2:985–992, 1990.
Nachemson et al., Growth Factors 3:309–316, 1990.
Cordeiro et al., Plastic and Reconstructive Surgey 83:1013–1019.

* cited by examiner

NERVE REGENERATION

This is a continuation of application Ser. No. 07/797,315, filed Nov. 25, 1991, now abandoned.

BACKGROUND OF THE INVENTION

This application relates to nerve regeneration by the administration of growth factors.

Growth factors are polypeptide hormones which stimulate a defined population of target cells. Examples of growth factors are platelet-derived growth factor (PDGF), insulin-like growth factors (IGF's), transforming growth factors beta (TGF-β), and alpha (TGF-α), epidermal growth factor (EGF), acidic fibroblast growth factor (aFGF), basic FGF (bFGF), and nerve growth factor (NGF).

The application of a combination of PDGF and IGF-I or PDGF and IGF-II in wound healing and bone regeneration has been described (Lynch et al, 1987, Proc. Nat'l. Acad. Sci. USA. 84:7696–7700; Lynch et al, 1989, J. Clin. Invest. 84:640–646; Lynch et al, 1989, J. Clin. Periodontol, 16:545–588; Lynch et al, 1991, J. Periodontol; 62:458–467. U.S. Pat. Nos. 4,861,757 and 5,019,559, hereby incorporated by reference).

IGF's, or somatomedins, are polypeptides of about 7.5 KD that have a strong homology to human proinsulin (Humbel, 1984 in Hormonal Proteins and Peptides 12:57–79). IGF-I and II share a 62% sequence homology. Their actions are mediated through two distinct receptors. The IGF-I receptor is named type-I receptor (IGF-IR), and the IGF-II receptor is named type-II receptor (IGF-IIR). The IGF-IR is a transmembrane protein structurally related to the insulin receptor (Ullrich et al, 1986 EMBO J. 5:2503–2512). It contains an extracellular binding domain consisting of two α-subunits and an intracellular tyrosine kinase domain consisting of two β-subunits. The type-I receptor has a high affinity for IGF-I and a lower affinity for IGF-II and insulin. The type II receptor is distinct from the IGF-I and insulin receptors (Morgan et al, 1987 Nature 329:301–307). It has a high affinity for IGF-II, a low affinity for IGF-I and it does not bind insulin. It is a transmembrane protein with a large extracellular binding domain and it does not seem to process tyrosine kinase activity. Its primary sequence is identical to that of the cation-independent mannose-6-phosphate receptor (Morgan et al, 1987 ibid). In addition to IGF-I and IGF-II, a truncated form of IGF-I has been obtained from brain and was named IGF-III (Sara et al, 1986; Proc. Nat'l. Acad. Sci.: USA; 83:4904–4907). IGF-III is lacking the three amino-terminal amino acid residues of IGF-I, but it retains functional properties similar to those of IGF-I. In vitro, IGF's exert diverse metabolic activities and they act as growth factors on a variety of cells including cells of mesenchymal origin (Froesch et al, 1985 Ann. Rev. Physiol. 47:443–467; Van Wyk, (1984) Hormonal proteins and peptides; 12: 81–125; Daugheday and Rotwein. Endocrine Rev. 1989; 10:68–91; Baxter et al (1985) Comp. Biochem. Physiol. 91β:229–235; Baskin et al (1988) TINS 11:107–111). IGF-I was also shown to be a potent inducer of oligodendrocyte development (McMorris et al, Proc. Natl. Acad. Sci. USA, 1986; 83:822–826) and a mitogen for cultured neonatal rat astroglial cells (Han et al, J. Neurosci. 1987; 7:501–506).

High levels of expression of IGF-I and IGF-II have been reported in fetal and neonatal tissues including brain (Han et al, J. Clin. Endocrinol Metab, 1988; 66:422–426; Schofield and Tate, 1987; Development 101:793–803; D'Ercole and Underwood, Pediar. Pulmonol, 1985; 1:599–606; D'Ercole (1987) J. Devel. Physiol. 9:481–495; Bondy et al. (1990), Mol. Endocrinol. 4:1386–1398).

IGF's have been suggested to act as neurotrophic factors in vitro (Aizenman et al, Brian Res. 1987; 406:32–42; Bothwell, J. Neurosci. Res. 1982; 8:225–231; European Patent Application No. 86850417.6; Recio-Pinto et al, J. Neurosci 1986; 6:1211–1219; Shemer et al, J. Biol Chem. 1987; 262:7693–7699) and in vivo (Hansson et al, Acta Physiol. Scand. 1986; 126:609–614; Anderson et al, Acta Physiol. Scand. 1988; 132:167–173; Kanje et al, Brain Res. 1988; 475:254–258; Sjoberg and Kanje, Brain Res. 1989; 485:102–108; Nachemson et al, Growth Factors 1990; 3:309–314) and to affect growth of undifferentiated neurons (Re-cio-Pento et al, J. Neurosci. Res. 1988; 19:312–320; Matteson et al.(1986) J. Cell Biol. 102:1949–1954). Addition of IGF-I or IGF-II alone or in combination with NGF appears to enhance in vitro the survival of neuronal cells (European Patent Application No. 63196524). Local administration of IGF-I to injured rat sciatic nerve has been reported to promote nerve regeneration (Hansson et al, 1986; Sjoberg and Kenje, 1989; Nachemson et al, 1990). Immunohistochemistry studies with specific anti-IGF-I antisera demonstrated increased amounts of endogenous IGF-I expression in the nerve and within the Schwann cells of injured rat sciatic nerve in vivo (Hansson et al, Cell Tissue Res. 1987; 247:241–247; and Hansson-et al, Acta Physiol. Scand. 1988; 132:35–41).

No data have been previously reported on the effect of exogenous platelet-derived growth PDGF) alone or in combination with other biologically active agents on nerve regeneration in vivo. In situ hybridization and immunostaining of tissues with antigen-specific antisera has demonstrated high levels of PDGF-A chain mRNA and immunoreactive PDGF-A in the neurons of embryonic and adult mice (Yeh et al, Cell 1991; 64:209–216). In the same study, significantly weaker signals of the PDGF-A chain were observed in glial cells. In vitro Schwann cells in both short and long term culture possess PDGF receptors and synthesize DNA in response to PDGF. The receptors were found to be mostly of the β type and PDGF-BB homodimer (i.e. PDGF-2) was a more potent mitogen than PDGF-AA homodimer. It was suggested that PDGF-BB may stimulate Schwann cell proliferation in an autocrine manner during normal development. (Eccleston et al, Eur. J. Neurosci. 1990; 2:985–992.) PDGF-β type receptors have also been reported on newborn rat brain neurons in vivo and in vitro. In vitro continuous PDGF-BB treatment of primary rat brain cell cultures resulted in outgrowth of neurites and prolonged survival (Smits et al., Proc. Natl. Acad. Sci. USA 1991; 88:8159–8163). The mRNA for PDGF-A is found in cultured Type-I astrocytes and in perinatel rat brain (Richardson et al, Cell 1988; 53:309–319). Type-I astrocytes have been suggested to be a source of PDGF in the nervous system (Pring et al, EMBO J. 1988; 18:1049–1056). PDGF has also been implicated as a factor in the proliferation and differentiation of rat optic nerve 0-2A progenitor cells (Raff et al, Nature 1988; 333:560–562; Noble et al, Nature; 1988; 333:560–562). PDGF appears to have a role in the proliferation and development of glial cells in the central nervous system (reviewed in Raff M, Science 1989; 243:1450–1455).

Peripheral Nerve Repair

Injury to peripheral nerves induces profound changes in the nerve cell body, its processes, and its surroundings (reviewed by Seckel, 1990; Muscle & Nerve 13:785–800). Following injury, the central nerve cell body becomes swollen, the nissl substance is dispersed, and the nucleus is displaced peripherally. The central cell body synthesizes a host of new mRNA'a, lipids, and cytoskeletal proteins (Grafstein B, et al, in *Neuronal Plasticity*, Cotman CW (ed) 1978). In addition other growth associated proteins (GAP's) are synthesized. Although GAP's do not appear to initiate growth, they are an essential component of the regenerative response. Electrophysiologic changes occur in the cell body that indicate differentiation towards a more plastic or embryonic state permitting growth (Foehring et al, (1986) *J. Neurophysiol* 55:947–965; Gorden et al, in *Somotic and Autonomic Nerve-Muscle Interactions*, Burnstock et al, (ed's) 1983).

The proximal axonal segment undergoes a variable degree of traumatic degeneration following nerve injury. This degenerative process extends at a minimum back to the next node of Ranvier, or maximally may result is cell death. When cell death is not the sequela, the area of the first node of Ranvier proximal to the injury will give rise to the regenerating nerve sprout (Gordon et al, (eds) *Neurology and Neurobiology. The current status of peripheral nerve regeneration.* pp. 79–88,1988). Formation of the growth cone, a specialized cell structure for mobility, is required at the tip of the regenerating nerve fiber. This structure facilitates passage of the neurofilament through tissue by releasing proteins which degrade the tissue matrix (Krystosek et al, (1981) *Science* 213:1532–1534). Growth cones can also respond to chemotrophic molecules such as NGF in vitro (Gundesen et al, (1980) *J. Cell. Biol.* 87:546–554). It appears that axons are capable of precise and specific selection of pathways and targets of innervation and that axonal growth is not a random process (Dodd et al, (1988) *Science* 242:692–699). However, in conventional nerve repair the growth cone is often prevented from reaching the distal nerve stump by a zone of injury characterized by axonal debris and lack of Schwann cell basal lamina. The latter is necessary to provide guidance to the regenerating nerve fibers. The result is incomplete function and/or the formation of a neuroma (Hafteck et al, (1968) *J Anat.* 103:233–243).

Schwann cells play a critical role in peripheral nerve regeneration. The initial breakdown products of axons after injury stimulates Schwann cell proliferation in preparation for phagocytosis. The Schwann cell and its basal lamina also provide a supportive and possibly growth promoting microenvironment for the regenerating axon. Subsequently, a regenerating axon is required for differentiation of the Schwann cell and production of myelin for remyelination of the axon by the Schwann cell. Thus, the coordinate regrowth and differentiation of Schwann cells and neuronal elements is required for optimal restoration of the architecture and function of peripheral nerves.

A number of agents have been reported to enhance nerve regeneration in vitro or in vivo (table 1), including NGF, fibronectin, fibrin, laminin, acidic and basic fibroblast growth factors (aFGF and bFGF respectively) and IGF-I. It should be noted that only by in vivo evaluation can the effects of these factors on true regeneration of the nerve be evaluated. (Regeneration is defined as the restoration of the original structure and function of the damaged tissue.)
Enhancement of Nerve Regeneration In Vivo.

The regeneration chamber model (i.e. entubulation) has provided a valuable method for assessing potential nerve regenerative agents (Lundborg et al, (1979) *Brain Res.* 178:573–576; (Lundborg et al, (1980) *J. Hand Sura.* 5:35–38). In this model, the two ends of the damaged nerve are inserted and sutured into a pseudomesothelial-lined tube (e.g., of silicon) kept open by a stainless steel thread; the tube acts to "guide" the growth of the two ends of the nerve. This technique alone may have some therapeutic advantages over conventional nerve repair and nerve graft techniques (Seckel et al, (1986) *Plast. Reconstr. Surg.* 78:793–800). Perhaps one of this technique's greatest advantages is that an appropriate nerve guide allows for the introduction of growth promoting factors into its lumen where these factors can act on the damaged nerve potentially to enhance regeneration. According to Sekel 1990; ibid:

". . . the concept that growth-promoting agents could be introduced into the regenerative micro-environment in the guide lumen in a therapeutic regimen is most appealing."

Thus far data have been reported in this model using aFGF, laminin, fibrin matrix, a mixture of laminin, testosterone, ganglioside GM-1, and catalase, and IGF-I.

Addition of aFGF resulted in a significant increase in the number of axons growing across the guide and a greater number of primary sensory and motor neurons (Cordeiro et al, (1989) *Plast. Reconstr. Surg.* 83:1013–1020). Laminin was reported to enhance regeneration in the guide in 2 weeks but at 6 weeks nerve regeneration was inhibited (Madison et al, (1985) *Exp. Neurol.* 88:767–772). Modification of the acellular fibrin matrix resulted in an increase in the size of the regenerating axon, the speed of the regeneration process, and the distance which could be bridged (Williams et al, in *Neurology and Neurobiology. The Current Status of Peripheral Nerve Regeneration.* Gordon et al (ed's). 1988; pp 111–122; Williams et al, *J. Comp. Neuro.* 1985; 231:209–220). The mixtures of laminin, testosterone, GM-1, and catalase enhanced nerve regeneration in 16 weeks (Miller et al, *Brain Res.* 1987; 413:320–326). Continuous infusion of IGF-I into the chamber lumen increased the length of the regenerating axons compared to infusion of saline plus 1% bovine serum albumin (Nachemson et al, *Growth Factors*; 1990;3:309–314).

SUMMARY OF THE INVENTION

The invention features a method of promoting growth of a mammalian nerve by contacting the nerve with purified PDGF. Preferably, the PDGF is contacted with a nerve process, preferably of a peripheral nerve. As used herein, "growth" refers, most preferably, to increase in length of a functional nerve process, e.g., an axon. Growth can also include inducement of proliferation of nerve cells or Schwann cells. Preferably, PDGF is mixed with another factor, most preferably IGF-I, prior to administration or at the site of desired nerve growth.

The second factor can also be another growth factor such as NGF, fibronectin, fibrin, laminin, acidic or basic FGF, EGF, a TGF, or another of the IGF's, i.e., IGF-II or IGF-III. (Active fragments or analogs of any of the active molecules which bind specifically to the appropriate receptors are included in the invention.)

In particular, it has been found that the synergistic action of PDGF and IGF-I can stimulate the in vivo regeneration of injured peripheral nerves. The effects of the combination of PDGF and IGF-I on nerve regeneration in vivo have been found to be superior to those induced by the administration of purified PDGF alone or purified IGF-I alone. As described below, the synergistic effects of the combination of PDGF and IGF-I stimulated about a 7.0 fold increase in the length of regenerated myelinated axons. The combination of PDGF and IGF aids the regeneration of the injured nerve, at least in part, by promoting both the directional regeneration of myelinated axons and the growth of the Schwann cells.

Schwann cell proliferation is crucial for supporting axonal myelinated growth. Thus, the synergistic action of PDGF and IGF-I results in axonal growth, proliferation of Schwann cells, and myelin sheath formation, contributing to the formation of myelinated nerve growth. As described below, the regenerated nerve induced by the synergistic action of PDGF and IGF-I retains in vivo functional activity, as judged by the reflexes of lightly anesthetized animals in response to an induced fine pincett-pain test. Regeneration using the composition of the invention is more effective than that achieved in the absence of treatment (i.e. without administration of exogenous agents) or by treatment with purified PDGF alone or purified IGF-I alone.

In preferred embodiments, nerve process regenerating compositions are prepared by mixing PDGF and any other active components with a pharmaceutically acceptable carrier substance, e.g. saline supplemented with albumin or methyl cellulose gel. Most preferably, purified PDGF and IGF-I are combined in a weight-to-weight ratio of between 1:500 and 100;1, preferably between 1:250 and 50:1 and more preferably between 1:100 and 25:1. The purified PDGF may be obtained from human platelets and the purified IGF-I from human blood, or both may be obtained by recombinant DNA technology. Thus, by the terms "PDGF" and "IGF" we mean both platelet and plasma derived and recombinant materials of mammalian, preferably primate origin; most preferably, the primate is a human, but can also be a chimpanzee or other primate. The terms "PDGF" and "IGF" include analogs which elicit biological activities by binding to the PDGF or IGF receptors, respectively. Recombinant PDGF can be recombinant heterodimer, made by inserting into culture prokaryotic or eukaryotic cells DNA sequences encoding both A and B subunits, and then allowing the translated subunits to be processed by the cells to form heterodimer. Alternatively, DNA encoding just one of the subunits can be inserted into cells, which then are cultured to produce homodimeric PDGF (PDGF-1 (AA) or PDGF-2 (BB) homodimer.

The term "purified" as used herein refers to PDGF, IGF-I, or other factor which, prior to use or combination with the other, is 90% or greater, by weight, i.e., the component is substantially free of other proteins, lipids, and carbohydrates with which it is naturally associated.

A purified protein preparation will generally yield a single major band on a polyacrylamide gel. Most preferably, the purified factors used in the compositions of the invention are pure as judged by amino-terminal amino acid sequence analysis.

The compositions of the invention provides a fast, effective method for the in vivo regeneration of injured nerves. In particular, the PDGF/IGF-I combination enhances the growth of nerves compared to natural healing (i.e. no exogenous agent added) or pure PDGF or IGF-I alone. The synergistic effect of the composition promotes about a 7.0 fold increase in new functional nerve regeneration.

Other features and advantageous of the invention will be apparent from the following description of the preferred embodiments thereof, and from the claims.

DESCRIPTION OF THE PREFERRED EMBODIMENTS

The drawing is first described.

DRAWING

The FIGURE is a bar graph illustrating nerve regenerative effects of PDGF, alone or combined with IGF-I.

PDGF AND IGF-I

Damaged or injured nerves are treated, and regenerated, with PDGF/IGF mixtures prepared by combining pure PDGF and IGF. Recombinant human IGF-I is available at the Institute of Molecular Biology, Inc. (Boston, Mass.) and is commercially available from R and D Systems, Inc., (Minneapolis, Minn.), UBI (Lake Placid, N.Y.), and Kabi (Sweden). Purified human PDGF (recombinant PDGF-I and PDGF-2) are available at the Institute of Molecular Biology, Inc. (Boston, Mass.), and are commercially available from R and D Systems, (Minneapolis, Minn.), UBI (Lake Placid, N.Y.), and Genzyme Corporation (Boston, Mass.).

PDGF can also be made by recombinant DNA technology as follows:

Platelet-derived growth factor (PDGF) derived from human platelets contains two polypeptide sequences (PDGF-1(A) and PDGF-2(B) polypeptides; Antoniades, HN., and Hunkapiller, M. (1983) *Science* 220:963–965). PDGF-1 is encoded by a gene localized in chromosome 7(Betsholtz, C., et al, *Nature* 320:695–699), and PDGF-2 is encoded by the sis oncogene (Doolittle, R. et al, (1983) *Science* 221:275–277; Waterfield et al, (1983) *Nature* 304:35–39) localized in chromosome 22 (Dallas-Favera, R. (1982) *Science* 218:686–688). The sis gene encodes the transforming protein of the Simian Sarcoma Virus (SSV) which is closely related to PDGF-2 polypeptide. The human cellular c-sis also encodes the PDGF-2 chain (Johnsson et al (1984) *EMBO J* 3:2963; Rao, CD et al, (1986) *Proc. Natl. Acad. Sci. USA* 83:2392–2396). Because the two polypeptide chains of PDGF are encoded by two different genes localized in separate chromosomes, the possibility exists that human PDGF consists of a disulfide-linked heterodimer of PDGF-1 and PDGF-2, or a mixture of the two homodimers (homodimer of PDGF-1 and homodimer of PDGF-2), or a mixture of the heterodimer and the two homodimers. Recombinant preparation of biologically active PDGF-1, PDGF-2 and PDGF-1/PDGF-2 dimers and of their anologs can be obtained by introduction of cDNA clones encoding c-sis/PDGF-2, PDGF-1 or PDGF-1 and PDGF-2 genes into enkaryotic cells using appropriate expression systems (Institute of Molecular Biology, Inc., Boston, Mass.); U.S. Pat. No. 4776073 (Murray et al, I), Hannick et al, (1986) *Mol. Cell. Biol.* 6:1343–1348; King et al, (1985) *Proc. Natl. Acad. Sci. USA* 82:5295–5299; Clarke et al, (1984) *Nature* 308:464; Gazit et al, *Cell* 39:89–97). Expression of the biologically active dimeric v-sis protein product is ssv-infected NRK cells has been reported (Owen et al, (1984) *Science* 225:54–56). Expression in procaryotes produced biologically inactive single chain protein product (Devare et al, (1984) *Cell* 36:43–49; Wang and Williams (1984) *J. Biol. Chem.* 259:10645–10648). Refolding of the single chain produced by procaryotes into its dimeric form produced biologically active PDGF preparations (Hoppe et al, (1989) *Biochemistry* 28:2956–2960).

Mammalian cells in culture infected with the Simian Sarcoma Virus which contains the gene encoding the PDGF-2 chain were shown to synthesize the PDGF-2 polypeptide and to process it into disulfide-linked homodimers with molecular weights of about 35,000 and 24,000 (Robbins, K. et al, (1983) *Nature* 305:605–608). In addition, PDGF-2 homodimer reacts with antisera raised against human PDGF. Furthermore, the functional properties of the secreted PDGF-2 homodimer are similar to those of platelet-derived PDGF in that it stimulates DNA synthesis in cultured fibroblasts, it induces phosphorylation at the tyrosine residue of a 185 kd cell membrane protein, and it is capable of competing with human ($^{125}$I)PDGF for binding to specific cell surface PDGF receptors (Owen, A. et al, (1984) *Science* 225:54–56). Similar properties were shown for the sis/PDGF-2 gene product derived from cultured normal human cells (e.g. human arterial endothelial cells), or from human malignant cells expressing the sis/PDGF-2 gene (Antoniades, H. et al, (1985) *Cancer Cells* 3:145–151).

The identification and cloning of the gene encoding the PDGF-1 chain (Betsholt, et al, (1986) *Nature* 320: 695–699) allowed the expression of its biologically active homodimer and the demonstration that the homodimer has functional activities similar to those of human PDGF. Receptor binding studies have shown that the PDGF-2 homodimer binds with high affinity and the human PDGF heterodimer with lower affinity to PDGF receptor beta (PDGF-R β) (Hart et al, 1988; *Science* 240:1529–1531; Heldin et al, 1988; *EMBO J.* 7:1387–1393).

The PDGF-R β did not recognize the PDGF-1 homodimer; the latter was bound to a second receptor, the PDGF receptor alpha (PDGF-R α). This receptor also bound the other two isoforms, the human PDGF and the PDGF-2 homodimer with high affinity (Heldin et al, 1988, ibid), The PDGF-R α was cloned by Matsui et al (1989) *Science* 243:800–804, and by Claesson-Welsh et al (1989) *J. Biol. Chem* 264:1742–1747). This α receptor is structurally similar to the β receptor sharing a 40% sequence identity, with an external binding domain and an intracellular kinase domain (Yarden et al, (1986) *Nature* 323:226–232; Claesson-Welsh et al, (1989) *Proc. Natl. Acad. Sci. USA* 86:4917–4921.

Peripheral Nerve Regeneration

To determine the effectiveness of PDGF and IGF-I in promoting the in vivo regeneration of peripheral nerves, the following experiments were performed.

The procedures used in these studies represent a modification of the system described by Hansson and associates (Nachemson et al, (1990) *Growth Factors* 3:309–314). Male Sprague-Dawley rats (200–230g) were anesthetized by intraperitoneal injection of a solution containing saline, sodium-pentobarbital (60 mg/ml) and diazepam (5 mg/ml) in 1:1:2 volume proportions.

Experimental Model

A "T" shaped silicone tube communicating system was prepared with an inner diameter of 1.5 mm. The length of the left branch of the "T" was usually 15 mm but in some experiments it varied from 30 to 90 mm. The right branch of the "T" was about 15 mm and remained opened. The vertical branch of the "T" (40 mm) was connected to a min-osmotic Alzet 2002 pump (Alza, Palo Alto, Calif.), with a capacity of 213 μl volume and a delivery rate of 0.5 microliters per hour implanted subcutaneously in the dorsum of the rat.

Surgical Procedure

The sciatic nerve was transsected at mid-thigh level in anesthetized rats. The proximal stump was introduced 2 mm into one of the channels and sutured there with two 9:0 Ethilone sutures. The following treatments were performed in the five experimental groups.

Experiment #1: No treatment

This represents a control group with only the proximal stump of the sciatic nerve introduced into the left arm of the "T" shaped channel. The other two channels were left empty.

Experiment #2: Vehicle Delivery

In this control group the proximal sciatic nerve stump was inserted into the left branch of the "T" shaped chamber and the Alzet 2002 pump was connected to the vertical branch of the "T" shaped chamber. The third channel remained empty. The pump and channel were filled with saline containing 1% bovine serum albumin (BSA) (Sigma Chem. Co., St. Louis, Mo.). The pump actively delivered the vehicle at a rate of 0.5 microliters per hour for two weeks.

Experiment #3: Delivery of IGF-1 alone

This experiment was as described in experiment #2, except that the Alzet pump was filled with saline/1% BSA containing 100 nanograms of IGF-I per microliter. The pump, delivered 0.5 microliters or 50 nanograms IGF-I per hour for two weeks.

Experiment #4: Delivery of PDGF alone

This experiment was as described in experiment #2, except that the Alzet pump was filled with saline/1% BSA containing 2.0 nanograms PDGF-2(B) per microliter—the pump delivered 0.5 microliters or 1.0 nanogram PDGF per hour for two weeks.

Experiment #5: Delivery of a combination of PDGF and IGF-1

This experiment was as described in experiment #2, except that the Alzet pump was filled with saline/1% BSA containing 2.0 nanograms PDGF-2(B) per microliter and 100 nanograms IGF-1 per microliter. The pump delivered 0.5 microliters or 1.0 nanogram PDGF and 50 nanograms IGF-1 per hour for two weeks.

Purified human recombinant IGF-I and purified human recombinant PDGF-2 (B) homodimer were obtained from the Institute of Molecular Biology, Inc. Boston, Mass.

Functional Assessment of Nerve Regeneration

After two and four weeks from the initiation of each experiment (the latter time being 2 weeks after termination of delivery of test material) the animals were lightly anesthetized. The functional state of the regenerated nerve was assessed by gentle pinch testing along the tube with a fine pincett. Pain reflexes in the anesthetized rat revealed the positions of functional axons.

Histologic Assessment of Nerve Regeneration

Following assessment of the functional activity of the regenerating nerve, the animals are sacrificed and the silicone tubes with adherent mini-osmotic pumps removed and photographed. The mini-osmotic pump and the roof of the channels were excised. The chamber was immersed in a solution, containing 2.5% purified glutaraldehyde in 0.1M cacodylate buffer at pH 7.15 for at least 24 hrs. After postfixation in 1% osmium tetroxide and dehydration the tissue within the channels was divided into small sections and embedded in agar resin 100. Transverse sections, 1 μm thick, were prepared at defined levels in the channels. The sections were stained with methylene blue and azure II, and examined by light microscopy. The length and direction of the regenerated nerve was determined by the presence of myelinated axons at each level. Unmyelinated axons or Schwann cells were not considered in the evaluation of regeneration in this study. Selected specimens were prepared for electron microscopy on a LKB Ultratome V and examined in a jeol 100 CX electron microscope after being contrasted with uranyl acetate and lead citrate.

Results

Results are illustrated in the FIGURE.

1. Control Group #1—No Treatment (n=18)

There was no significant growth in any of the specimens in the control group, but mostly a retraction of the impaired nerve by about 1 mm. No functional recovery was observed in any of these animals. Immunohistochemical analysis of formalin-fixed sciatic nerves, processed for demonstration of neurofilaments, revealed that axons formed neuroma-like structures in the nerve but rarely entered the silicone-tube. If processed for demonstration of the Schwann cell marker protein S-100, it was evident that very few Schwann cells entered the silcone tube, which in stead was filled with liquid as well as fibrin and inflammatory cells.

2. Control Group #2—Treated with Vehicle Delivery (n=22)

There was no significant growth from the cut sciatic nerve receiving vehicle only, but rather a variable degree of retraction. No functional recovery was observed in any of these animals. Immunohistochemical analyzes of specimens processed for demonstration of neurofilaments, revealed that few axons entered the tube and that only few Schwann glial cells could be seen in the tube.

3. Control Group #3—Treated with IGF-I alone (n=17)

Delivery of IGF-I with a miniosmotic pump produced growth by regenerating sciatic nerve of 0.6±0.3 mm/day as measured for a two week period. The length of the axons corresponded about to that indicated by the pinch test. After 4 weeks numerous myelinated axons could be seen within the tube at distances corresponding to the above mentioned growth. Numerous Schwann cells could be demonstrated along the axons.

4. Group #4—Treated with PDGF alone (n=7; 4 with body weight as specified above. while 3 had a body weight of 450–490 g)

Delivery of PDGF alone with the miniosmotic pump produced growth by regenerating sciatic nerves of 0.2 to 0.7 mm/day. No distinct minifasciles formed by at least ten axons were identified. However, many slightly S-100 positive Schwann cells could be demonstrated, indicating stimulation of proliferation of these cells by the PDGF. There was no evidence of functional recovery.

5. Group #5—Treated with the combination of PDGF & IGF-I (n=7)

This group showed an impressive growth of functional nerve fibers. The average growth over a two week period was 4.2±0.7 mm per day.

After 4 weeks there was a larger number of large, myelinated axons than seen after any of the other treatments stated above. Numerous Schwann cells accompanied the axons. The functional recovery corresponded to the length of the axonal bundles, as judged by a gentle pinch testing along the tube system using a pincett, reflecting pain reflexes in the lightly anesthetized rats by "twitching" of the leg and nocioceptive reflexes.

Thus the effects of the combination of PDGF/IGF-I on nerve regeneration are synergistic, not additive, since PDGF alone had no significant effects on axonal growth and IGF-I stimulated only a small rate of growth. The growth of the myelinated nerve induced by PDGF/IGF-I was about 7-fold greater than that induced by IGF-I alone. PDGF did appear to stimulate proliferation of Schwann cells, an event of potentially significant benefit for treating demyelination diseases such as MS.

Medical Use

The results of these experiments indicate that diseases such as multiple sclerosis (MS) amyotrophic lateral sclerosis (ALS) or other neurodegenerative diseases resulting in damage to or atrophy of nerve processes may be treated with the compounds described herein. Furthermore, nerves damaged due to trauma may also-be regenerated by the compounds described herein.

The formulations of this invention may be administered parenterally for systemic distribution or locally at the site of the injured or damaged nerve. The compounds provided herein can be formulated into any pharmaceutically acceptable excipients or carrier.

When the intended use of the compounds is for the treatment of CNS disorders (e.g., ischemia, trauma, and tumors), of the brain or other regions of the CNS, (e.g., the retina), they may be made to contact the tissues of the CNS by direct infusion into the CNS or cerebrospinal fluid, conjugation with a molecule which naturally passes into the CNS, by reducing the overall length of the polypeptide chain and retaining the biologically active site, or by increasing the lipophilicity of the compounds, e.g., by appropriate amino acid substitutions.

Effective molar ratios of PDGF to IGF are anticipated to be between 1:500 and 100:1, preferably between 1:250 and 50:1, and more preferably between 1:100 and 25:1. Effective doses are anticipated to be 0.001 μg to 1,000 μg of active components per day of injured, damaged, or atrophied nerve.

Other embodiments are within the following claims.

TABLE 1

Factors reported to enhance nerve regeneration

| Factor | Type/Mechanism of action |
|---|---|
| Nerve growth factor (NGF) | Neuronotrophic factor (NTF) |
| Ciliary neuronotrophic factor (CNTF) | NTF |
| Motor nerve growth factor (MNGF) | NTF |
| Fibronectin | Neurite promoting factor (NPF) |
| Laminin | NPF |
| Neural cell adhesion molecule (N-CAM) | ? NPF |
| N-cadhenin | ? NPF |
| Fibrin | Matrix factor (MF) |
| Fibronectin | MF (Precursor) |
| Hormones | |
| Estrogen | Metabolic ? increased protein synthesis |
| Testosterone | Metabolic ? increased protein synthesis |
| Thyroid hormone | Metabolic ? increased protein synthesis |
| Corticotropin | Metabolic ? increased protein synthesis |
| Org. 2766 | Metabolic ? increased protein synthesis |
| Insulin | Metabolic ? increased protein synthesis |
| Catalase | Protection from peroxide damage |
| Acidic fibroblast growth factor (aFGF) | ? NTF |
| Basic fibroblast growth factor (bFGF) | ? NTF |
| Forskolin | Increased protein synthesis |
| Glia-derived protease inhibitor (GdNPF) | ? NPF |
| GM-1 Gangliosides | ? |
| Insulinlike growth factor | ? NTF |
| Isaxonine | Increased axonal transport, increased polymerization of tubulin |
| Leupeptin | Inhibits traumatic degeneration |
| Muscle basal lamina | ? NPF ? NTF |
| Pyronin | Speeds wallerian degeneration |
| Conditioning lesion | Earlier wallerian degeneration |
| Electrical stimulation | ? |
| de Medinaceli technique | Minimize traumatic degeneration |

What is claimed is:

1. A method of promoting regeneration of a peripheral nerve in a mammal comprising contacting said nerve with purified platelet-derived growth factor (PDGF) and a second purified growth factor selected from the group consisting of insulin-like growth factor-I (IGF-I) and acidic fibroblast growth factor (aFGF).

2. The method of claim 1, wherein said PDGF and said second factor are contacted with said peripheral nerve.

3. The method of claim 1, wherein said second factor is IGF-I, which is administered simultaneously with said PDGF or close enough in time to said PDGF administration so that the two act synergistically to promote peripheral nerve regeneration.

4. The method of claim 3 wherein said IGF-I and PDGF are admixed together in a physiologically acceptable carrier prior to administration.

5. The method of claim 2 wherein said nerve comprises a damaged myelinated axon, and said method further promotes myelination of said axon.

* * * * *